United States Patent [19]

Phillips et al.

[11] 4,134,924

[45] Jan. 16, 1979

[54] PREPARATION OF 2-CYCLOPENTENYL ETHERS

[75] Inventors: Benjamin Phillips, Riverside, Conn.; Walter J. Skraba, White Plains, N.Y.

[73] Assignee: Union Carbide Corporation, New York, N.Y.

[21] Appl. No.: 823,750

[22] Filed: Aug. 11, 1977

[51] Int. Cl.$^2$ .............................................. C07C 41/00
[52] U.S. Cl. ...................................... 568/664; 560/231; 568/838
[58] Field of Search ....................................... 260/611 R

[56] References Cited

U.S. PATENT DOCUMENTS

| | | | |
|---|---|---|---|
| 2,847,477 | 8/1958 | Watanabe et al. | 260/611 |
| 2,898,378 | 8/1959 | Young | 260/611 R |
| 3,250,814 | 5/1966 | Stephenson | 260/611 R X |
| 3,301,887 | 1/1967 | Kirshenbaum | 260/462 |
| 3,346,623 | 10/1967 | Young | 260/497 |
| 3,471,532 | 10/1969 | Young | 260/410.9 |
| 3,577,466 | 5/1971 | Nozaki | 260/611 R X |
| 3,641,159 | 2/1972 | Schmerling | 260/611 R |

*Primary Examiner*—Bernard Helfin
*Attorney, Agent, or Firm*—Bernard Francis Crowe

[57] ABSTRACT

Bis-(2-cyclopentenyl) ethers are prepared by contacting a 2-cyclopentenyl carboxylate or 2-cyclopentenol with an aqueous acid solution having a pH in the range of about 1.0 to about 3.0.

14 Claims, No Drawings

PREPARATION OF 2-CYCLOPENTENYL ETHERS

BACKGROUND OF THE INVENTION

This invention pertains to the preparation of bis-(2-cyclopentenyl)ether from 2-cyclopentenyl carboxylates and/or 2-cyclopentenol as well as mixed ethers.

Bis-(2-cyclopentenyl) ether when epoxidized affords a commercial cycloaliphatic epoxide as described in U.S. Pat. Nos. 2,973,373. The use of this epoxy resin is described in U.S. 2,935,488.

Bis-(2-cyclopentenyl)ether was first synthesized by David et al. [Bull. Soc. Chim. France (5) 11, 5614 (1944)] employing the procedure shown below:

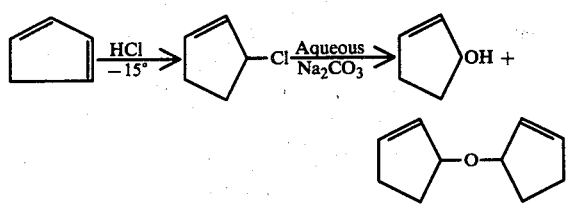

Several features of the above synthesis make it costly to conduct on a commercial scale. Expensive corrosion-resistant equipment is required in both steps because the process employs hydrogen chloride as a reactant and produces sodium chloride as a by-product. Chloride ion even in neutral or basic medium, causes severe pitting of stainless steel. Secondly stoichiometric amounts of both HCl and base are consumed which adds to the cost of the products. Thirdly malodorous by-products are formed contaminating the waste aqueous salt solution and producing unpleasant air-borne odors.

When one attempts to add a weak acid such as water or acetic acid to the double bond system of cyclopentadiene no formation of the desired 2-cyclopentenyl compound is observed, and the eventual sole product is dicyclopentadiene. This dimerization requires no catalyst.

When a strong acid other than anhydrous HCl or HBr is used, either in stoichiometric or catalytic amounts, a rapid polymerization of cyclopentadiene occurs.

DESCRIPTION OF THE INVENTION

A method which avoid the corrosion problems inherent in the use of hydrogen halides, does not require a stoichiometric amount of base, produces no inorganic by-products or malodorous waste streams, and can be conducted to produce bis-(2-cyclopentenyl) ether in high chemical efficiency has been developed which comprises contacting one part by weight of at least one 2-cyclopentenyl derivative having the formula:

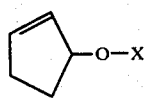

wherein x is

or H and R is R is H or an alkyl or cycloalkyl having one to about eight carbons or aryl having six to ten carbons, with about 0.1 to about 10 parts by weight of an aqueous solution containing about 0.01 to about 2.0 moles per liter of solution of an acid having a pKa of about 2 to about 3, at a temperature of about 0° C. to about 100° C.

The 2-cyclopentenyl derivative may be either an ester or an alcohol. The preparation of both of these 2-cyclopentenyl derivatives has been described in the literature. Thus for example, Gilmore et al. in the Journal of the Chemical Society, 1971, 2355-7, describes the preparation of 2-cyclopentenyl acetate in 70 percent yield by the interaction of cyclopentene with acetic acid using stoichiometric amounts of manganic acetate or potassium permanganate. Shono et al. [Tetrahedon Letters, 59, 6207-8 (1968)] describes the anodic oxidation of cyclopentene in acetic acid in a 41% yield. Dane et al. [Ann. 532, 28-39 (1937)] prepared 2-cyclopentenyl acetate from cyclopentene, selenium dioxide and acetic anhydride. Dane et al. [Ann. 539, 207-12 (1939)] obtained 2-cyclopentenyl acetate from cyclopentene, lead tetraacetate and acetic acid. U.S. Pat. No. 3,632,633 issued to Louvar discloses the preparation of 2-cyclopentenyl acetate from cyclopentene and acetic acid over a zeolite catalyst.

Baltz et al.[East German 81650]obtained 2-cyclopentenol from cyclopentene and tertiary-butyl hydroperoxide in the presence of a rhodium catalyst. Criegee et al. [Ber. 721, 1799 (1939)] oxidized cyclopentene with oxygen and ultraviolet light to the corresponding hydroperoxide which was then reduced with sodium sulfite to the corresponding 2-cyclopentenol.

Where a cyclopentenyl ester is used as the starting material, it is preferred that R be methyl, that is, the product derived from cyclopentene and acetic acid. However other acids may also be used such as formic, propionic, butyric, valeric, hexanoic, heptanoic, octanoic, isobutyric, benzoic, cyclohexanecarboxylic acids and the like.

As a variation of this reaction mixed 2-cyclopentenyl ethers may be obtained by adding an equivalent amount of a primary or secondary alcohol as part of the charge. Primary aliphatic alcohols having about 1 to 4 carbon atoms are preferred. These are exemplified by allyl alcohol, methallyl alcohol, ethyl alcohol, n-propyl alcohol, n-butyl alcohol and the like. Secondary alcohols afford lower yields than primary alcohols but can be used. The secondary alcohols can be aliphatic or cycloaliphatic, as for example, isopropyl alcohol, 2-butanol, cyclohexenyl alcohol, and the like. Tertiary alcohols, however, do not serve as suitable substrates in this reaction.

It was surprising to observe that the mixed 2-cyclopentenyl ethers can be prepared with a high degree of specificity because for some reason, not understood, the addition of the primary or secondary alcohol to the reaction mixture inhibits the formation of bis-(2-cyclopentenyl) ether, allowing a higher yield of a single product ether.

Although a ratio of about 0.1 to about 10 parts by weight of the aqueous acid solution can be used per part of the 2-cyclopentenyl derivative, it is preferred to use a range of about 0.2 to about 3 parts by weight of aqueous solution.

Although the concentration of acid can range from about 0.01 to about 2.0 moles per liter of solution, it is preferred to use a range of about 0.05 to about 0.5 moles of acid per liter of solution.

Aqueous solutions are derigueur since it was unexpectedly found that in the absence of water little or no ether is formed.

Although the reaction can be run at a temperature of about 0° C. to about 100° C., the preferred range is about 10 to about 50° C.

Pressure is not narrowly critical and so while it is preferred to carry out the claimed method at atmospheric pressures for economic reasons, it can also be run at superatmospheric or subatmospheric pressures if desired.

Time is not narrowly critical but for commercial applications reaction times of about 1 to 3 hours are found to be convenient affording satisfactory yields of bis-(2-cyclopentenyl) ether or mixed ethers. The time required depends on the temperature and the particular catalyst solution used.

The acid concentrations used in the claimed method afford aqueous solutions with a pH in a range of about 1 to about 3. This is a critical factor required to prevent the formation of cyclopentadiene polymers as an undesirable side reaction, which is favored by strong acids. The acidic compounds used to afford this range of pH cover a wide spectrum of materials. Thus, for example, one can use alkali metal bisulfates and other bisulfates, oxalic acid, maleic acid, fumaric acid, sulfamic acid, trichloroacetic acid, picric acid, Lewis acids such as boron trifluoride and the like which are hydrolytically stable, and acid salts of primary, secondary or tertiary amines and quarternary ammonium hydroxides with di- or polybasic acids. Illustrative acid salts are: pyridinium bisulfate, triamylammonium bisulfate, benzyltrimethylammonium bisulfate, tetrabutylammonium bisulfate, tetrabutylammonium hydrogen m-benzenedisulfonate, tetrabutylammonium pyrophosphate, partial trioctylammonium salts of polyphosphoric acid, and the like. Other acidic compounds having ionization constants in the range of about $1 \times 10^{-2}$ to about $1 \times 10^{-3}$ i.e., a pKa of about 2 to about 3, will be readily apparent to those skilled in the art can also be used.

As a variation of this method one can go through a hydrolysis or alcoholysis step converting 2-cyclopentenyl ester to 2-cyclopentenol before conversion to the desired product, bis-(2-cyclopentenyl) ether.

The invention is further described in the examples which follow. All parts and percentages are by weight unless otherwise specified.

The terms "conversion", "yield" and "chemical efficiency" are used herein according to the following definitions:

$$\text{Conversion (\%)} = \frac{S_f - S_r}{S_f} \times 100$$

$$\text{Yield (\%)} = \frac{P}{S_f} \times 100$$

$$\text{Chemical efficiency} = \frac{P}{S_f - S_r - I_r} \times 100$$

$S_f$ = Mols of starting material fed to the reactor.
$S_r$ = Mols of starting material remaining at the end of the reaction.
$P$ = Mols of product formed.
$I_r$ = Mols of any intermediates remaining at the end of the reaction.

EXAMPLE 1

2-CYCLOPENTENYL ACETATE BY OXIDATION OF CYCLOPENTENE WITH t-BUTYL HYDROPEROXIDE IN ACETIC ACID

To a 500 ml heavy glass bottle containing a magnetic stirring bar was added 1.0 g (0.005 mol) of cuprous acetate and 60.0 g (1.0 mol) of acetic acid. The mixture was stirred to dissolve the salt. Then 68.0 g. (1.0 mol) of cyclopentene, 31.9 g (0.33 mol) of 93.8 percent t-butyl hydroperoxide, and an accurately weighed amount of chlorobenzene as an internal standard were added. The bottle was capped, and the reaction mixture was stirred at 70° C. for 20 hours and the contents then analyzed by gas chromatography using an OV-17 column [50% phenylmethylsilicone on an inert support] temperature programmed for 80–220° C. at 8° per minute. Quantification of results was accomplished by relating the chromatographic peaks to that of the chlorobenzene and taking into consideration the response factors previously determined with authentic samples of the individual components of the reaction mixture. The analysis showed a 65% yield of 2-cyclopentenyl acetate and a 4.3% yield of 2-cyclopentenol. Only small amounts of 3 unknown compounds were present. In order to determine if any resinous or high-boiling by-products not detectable by gas chromatography had formed, the crude reaction product mixture was flash distilled in a rotary evaporator at a flask temperature of 140° C. and a final pressure of 10 torr. The weight of the residue was approximately equal to the weight of cuprous acetate catalyst that had been used in the reaction. This demonstrated that only a very small amount of organic residue had been formed.

EXAMPLE 2

ISOLATION OF 2-CYCLOPENTENYL ACETATE

Nine preparations of 2-cyclopentenyl acetate were conducted using the amounts of starting materials and the conditions described in Example 1 with the omission of the chlorobenzene internal standard. The crude products were combined and stripped of unreacted cyclopentene by distillation in a rotary evaporator. The remaining material was flash distilld rapidly under reduced pressure to eliminate the copper catalyst and any high-boiling residues and was then fractionally distilled through a spinning band column. Cyclopentenyl acetate, assaying 97.8% purity by gas chromatography, was isolated as a fraction boiling at 40° C. at 8 torr and having a refractive index ($n_D^{25}$) of 1.4455. The total yield of 2-cyclopentenyl acetate in the distillation fractions was 65% of the theoretical.

EXAMPLE 3

2-CYCLOPENTENOL BY METHANOLYSIS OF 2-CYCLOPENTENYL ACETATE USING SODIUM METHYLATE CATALYST

To a test tube containing a mini magnetic stirring bar was added 500 mg (3.9 millimoles) of 2-cyclopentenyl acetate and a sodium methylate solution prepared by dissolving 9.2 mg (0.4 mollimoles) of sodium metal in 800 ml mg (25 millimoes) of methanol. The tube was stoppered and the solution stirred at 40° C. for 2 hours.

To the solution was then added a weighed amount of 1,4dioxane to serve as a chromatographic standard, and the mixture was then analyzed by gas chromatography using an "Apiezon" column, temperature programmed from 80° to 220° C. at 8° per minute. The analytical results, corrected for response factors of the components, showed that 2-cyclopentenol had been formed in a yield of 99%. Methyl acetate was formed as the coproduct. The data of this Example are recorded in Table 1 below.

EXAMPLE 4–8

The procedure in Example 3 was repeated using the following methanolysis catalysts: magnesium methylate, sodium hydroxide, calcium oxide, and Dowex 1-X4 in the methoxide form. Dowex 1-X4 is an anion exchange resin sold in the chloride form. To convert it into the methoxide form it was placed in a burette and subjected to a continuous flow of sodium methylate solution until the effluent gave a negative test for chloride ion. Dry methanol was then passed through the bed to eliminate residual sodium methylate. The resin was stored with methanol. In Example 8 Dowex 1-X4 was used in the hydroxide form. This was prepared by treating the chloride form with an aqueous solution of sodium hydroxide and then passing dry methanol through the resin solumn to eliminate sodium hydroxide and water. The data of Examples 4–8 are recorded in Table 1 below.

with sufficient acetone to solubilize the mixture. Analysis of the products was carried out by gas chromatography using an "Apiezon" column at 80–220° C., temperature programmed at 8° per minute. Bis-(2-cyclopentenyl) ether was obtained in a yield of 88 percent and an efficiency of 99 percent. Pertinent data are recorded in Table II.

EXAMPLE 10

ETHERIFICATION OF 2-CYCLOPENTENOL USING AQUEOUS SODIUM BISULFATE CATALYST

Example 9 was repeated with the exception that sodium bisulfate was used as the catalyst in place of tetrabutylammonium bisulfate. Pertinent data are recorded in Table II.

CONTROL A

ETHERIFICATION OF 2-CYCLOPENTENOL USING DRYING TETRABUTYLAMMONIUM BISULFATE CATALYST

Example 9 was repeated with the exception that dry tetrabutylammonium bisulfate was used as the catalyst. No reaction occurred. It is thus evident that water is necessary for the reaction even when the starting material is a 2-cyclopentenol rather than a 2-cyclopentenyl ester. Pertinent data are recorded in Table II.

TABLE II

Etherification of 2-Cyclopentenol
(All reactions conducted at 40° C for 3 hrs)

| Example Number | Catalyst Type | Catalyst g | mM[1] | H$_2$O g | H$_2$O mM | 2-Cyclopentenol g | 2-Cyclopentenol mM[1] | Bis-(2-cyclopentenyl) ether Yield % | Efficiency % |
|---|---|---|---|---|---|---|---|---|---|
| 9 | Bu$_4$NHSO$_4$ | 0.02 | 0.06 | 0.25 | 14 | 0.3362 | 4.0 | 87.8 | 99.1 |
| 10 | NaHSO$_4$ | 0.007 | 0.06 | 0.30 | 17 | 0.2776 | 2.7 | 32.6 | 41.2 |
| Control A | Bu$_4$NHSO$_4$ | 0.02 | 0.06 | none | | 0.2304 | 2.7 | no reaction | |

[1]Millimoles.

TABLE I

2-Cyclopentenol by Methanolysis of 2-Cyclopentenyl Acetate

| Example Number | Catalyst Type | mM | Methanol mM | CPOAc mM | Time (hrs) | Temp. °C | CPOH mM | Yield % |
|---|---|---|---|---|---|---|---|---|
| 3 | NaOCH$_3$ | 0.4 | 25 | 3.94 | 2 | 40° | 3.91 | 99 |
| 4 | Mg(OCH$_3$)$_2$ | 0.3 | 15 | 3.90 | 18 | 40° | 2.85 | 73 |
| 5 | NaOH | 0.4 | 16 | 4.03 | 1 | 40° | 3.66 | 91 |
| 6 | CaO | 0.2 | 43 | 3.84 | 2 | 40° | 3.65 | 97 |
| 7 | Dowex+$^{OCH_3-}$ | 0.2g(dry)* | 44 | 3.99 | 2 | 40° | 3.68 | 94 |
| 8 | Dowex+$^{OH-}$ | 0.05g(dry)* | 10 | 3.98 | 2 | 40° | 3.82 | 96 |

CPOAc = 2-Cyclopentenyl acetate
CPOH = 2-Cyclopentenol
*Dowex catalyst was added to reaction mixture wet. The dry weight was determined by filtering off the catalyst at the end of the run and drying and weighing it.

EXAMPLE 9

ETHERIFICATION OF 2-CYCLOPENTENOL USING AQUEOUS TETRABUTYLAMMONIUM BISULFATE CATALYSTS

To a test tube with a mini magnetic bar was added 0.02 g (0.06 millimoles) of tetrabutylammonium bisulfate and 0.25 g (14 millimoles) of water. The bisulfate was first dissolved in the water, and then 0.336 g (4.00 millimoles) of 2-cyclopentenol was added. The test tube was stoppered and the mixture was stirred at 40° C. for 3 hours.

For quantitative analysis of the products, a weighed amount of dioxane (internal standard) was added along

EXAMPLE 11–13

BIS-(2-CYCLOPENTENYL) ETHER FROM 2-CYCLOPENTENYL ACETATE (one-step)

In a series of small-scale experiments, 0.5 gram samples of 2-cyclopentenyl acetate were stirred with aqueous solutions of tetrabutylammonium bisulfate. At the end of the reaction period, dioxane (internal standard) was added in weighed amounts. Acetone was added to convert the two layers of the reaction mixture into a single phase. The resulting solution was analyzed by gas chromatography. The results are given in Table III.

EXAMPLE 14

BIS-(2-CYCLOPENTENYL ETHER) FROM 2-CYCLOPENTENYL ACETATE (one-step)

2-Cyclopentenyl acetate (9.9 grams, 79 millimoles) was added to a solution of tetrabutylammonium hydrogen sulfate (0.40 grams, 1.23 millimoles) in 10 grams of water. The mixture was stirred at 40° C for 6 hours, and the two layers were then separated and analyzed using the previously described technique of employing 1,4-dioxane as an internal standard. Sulfur analysis to determine distribution of tetrabutylammonium hydrogen sulfate between the two layers was conducted by x-ray fluorescence. The analytical results are summarized below. (The following conventions are used: mM=millimoles, CPOH = 2-cyclopentenol; CPE = bis-(2-cyclopentenyl) ether; and CPOAc=2-cyclopentenyl acetate).

|  | Tetra-butyl-ammonium hydrogen sulfate | Acetic Acid | CPOH | CPE | CPOAc |
|---|---|---|---|---|---|
| Oil Layer | 0.02 mM | 15.0 mM | 10.4 mM | 29.8 mM | 16.1 mM |
| Water Layer | 1.28 mM | 44.6 mM | 6.2 mM | 0.6 mM | 1.4 mM |
| Total | 1.30 mM | 59.6 mM | 16.6 mM | 30.4 mM | 17.5 mM |

These data demonstrate that essentially all of the tetrabutylammonium hydrogen sulfate catalyst remained in the aqueous layer. Thus, the aqueous layer could be recycled after removal of at least part of the acetic acid (by extraction or other suitable means). The extract can then be combined with the oil layer for isolation of the cyclopentenyl ether by distillation. Fractions containing 2-cyclopentenol and/or 2-cyclopentenyl acetate can be recycled to the etherification reaction.

EXAMPLES 15–23

Bis-(2-cyclopentenyl ether) from 2-cyclopentenyl acetate

The procedure described for Examples 11–13 was employed for evaluation of various catalysts for the one-step conversion of 2-cyclopentenyl acetate to bis-(2-cyclopentenyl) ether. The results are presented in Table IV.

TABLE IV

Bis-(2-cyclopentenyl)ether from 2-cyclopentenyl acetate

| Example No. | (g) | H₂O (g) | Catalyst (g) | pH | Time (hrs) | Temp | Conv (%) | Yield (%) | Eff (%)* |
|---|---|---|---|---|---|---|---|---|---|
| 15 | 0.5 | 0.25 | oxalic acid 0.006 | 1.3 | 3.0 | 40° | 63 | 29 | 71 |
| 16 | 0.5 | 0.25 | Picric acid 0.014 | 1.6 | 3.0 | 40° | 71 | 21 | 47 |
| 17 | 0.5 | 0.25 | Maleic acid 0.08 | 1.9 | 3.0 | 40° | 61 | 21 | 49 |
| 18 | 0.5 | 0.25 | BF₃ . Et₂O 0.01 | 1.9 | 5.0 | 24° | 86 | 16 | 34 |
| 19 | 0.5 | 0.25 | H₃PO₄ 0.0033 | 1.9 | 4.0 | 40° | 73 | 16 | 26 |
| 20 | 0.5 | 0.25 | HCL 0.0035 | 1.3 | 2.0 | 40° | 70 | 30 | 63 |
| 21 | 0.5 | 0.25 | Bu₄NHSO₄ 0.020 | 1.6 | 5.0 | 24° | 30 | 7 | 99 |
| 22 | 0.5 | 0.25 | Bu hd 4NHSO₄ 0.020 | 1.6 | 18.0 | 24° | 60 | 37 | 98 |
| 23 | 0.5 | 0.25 | Cl₃CCOOH 0.01 | 1.2 | 3 | 40° | 66 | 17 | 51 |

*Efficiencies are calculated on basis of taking credit for co-produced 2-cyclopentenol as a starting material.

TABLE III

Bis-(2-Cyclopentenyl) Ether from 2-Cyclopentenyl Acetate Using Bu₄NHSO₄ Catalyst

| Example No. | Charge | | | Conditions | | Yield | | Efficiency* to bis-(2-cyclopentenyl) ether |
|---|---|---|---|---|---|---|---|---|
| | CPOAc | H₂O | Bu₄NHSO₄ | Temp | Time | Bis-(2-cyclopentenyl) ether | 2-cyclopentenol | |
| 11 | 0.5g | 1.0g | 0.02g | 40° | 3 hrs. | 41.6% | 35.0% | 96.0% |
| 12 | 0.5g | 0.25g | 0.02g | 24° | 20 hrs. | 40.4% | 31.6% | 89.7% |
| 13 | 0.5g | 0.25g | 0.02g | 40° | 4 hrs. | 33.7% | 24.4% | 82.5% |

*Efficiency calculations take credit for 2-cyclopentenol as an intermediate since it can be recycled for production of additional ether.

EXAMPLE 24

Alcoholysis of 2-cyclopentenyl acetate and etherification of 2-cyclopentenol to bis-(2-cyclopentenyl) ether.

This reaction was carried out in two steps but without the intermediate isolation of 2-cyclopentenol. In the first step, 2-cyclopentenyl acetate was converted to 2-cyclopentenol using a basic catalyst as described in Example 8. In the second step the 2-cyclopentenol was converted to bis-(2-cyclopentenyl) ether using an acidic catalyst.

Step 1: To a 50 ml. round-bottom flask with a magnetic stirring bar was added 9.92 grams (78.7 mols) of 2-cyclopentenyl acetate, 29 grams of methanol and 0.75 grams of Dowex 1-X4 resin in the methoxide form. The flask was stoppered and the contents stirred at 40° C. for 2.5 hours. Gas chromatographic analysis showed that 2-cyclpentenol was formed in greater than 95 percent yield. The resin catalyst was removed by filtration, and the product solution was stripped at 60° C. under vacuum to remove the unreacted methanol and the methyl acetate formed. Gas chromatographic analysis showed that approximately 10 percent of the methanol was still present in the residue.

Step 2: To the 50 ml round-bottom flask containing the residue (6.8 grams) from the distillation in step 1 was added 5 grams of water and 0.5 grams of tetrabutyl ammonium hydrogen sulfate. The flask was stoppered and the contents stirred at 40° C. for 3 hours. To the flask was then added chlorobenzene as an internal standard and acetone to solubilize the mixture. Gas chromatographic analysis was carried out through an OV-17 column, at 80-220° C., temperature programmed at 8° per minute. The results showed a 61.1 percent yield of bis-(2-cyclopentyl) ether, a 12.2 percent yield of 2-cyclopentenol, 2.5 percent of unreacted 2-cyclopentenyl acetate, and the remaining 24 percent as 2-cyclopentenyl methyl ether that was formed by the reaction of methanol (present in the residue from distillation) with 2-cyclopentenol.

2-Cyclopentenol reacts with methanol in the presence of an acidic catalyst forming 2-cyclopentenyl methyl ether. By eliminating the methanol completely in the stripping operation at the end of Step 1, a higher yield of bis-(2-cyclopentenyl) ether can be produced.

CONTROL B

ATTEMPTED ETHERIFICATION OF ALLYL ALCOHOL USING AQUEOUS TETRABUTYLAMMONIUM BISULFATE CATALYST

To 5.0 g of allyl alcohol was added a solution of 0.20 g of tetrabutylammonium bisulfate in 6.0 g of water. The clear solution was heated under reflux (90° C) for 16 hours. The mixture was then cooled and analyzed by gas chromatography using an Apiezon column programmed from 80° to 220° C. The only peak exhibited was that for allyl alcohol. No diallyl ether had been formed.

EXAMPLE 25

ALLYL 2-CYCLOPENTENYL ETHER FROM ALLYL ALCOHOL AND 2-CYCLOPENTENYL ACETATE USING AQUEOUS TETRABUTYLAMMONIUM BISULFATE CATALYST

To a mixture of 2-cyclopentenyl acetate (0.3 g, 2.4 millimols) and allyl alcohol (0.5 g, 8.6 millimols) was added a solution of 0.02 g of tetrabutylammonium bisulfate in 0.3 g of water. The mixture, in a stoppered test tube, was stirred magnetically while being heated at 40° C for 3 hours. At the end of this reaction period, acetone was added to produce a homogeneous solution for analytical purposes, and a sample was examined by gas chromatography using a "Carbowax-20M" column programmed from 80° to 220° C. The following peaks were observed:

| COMPOUND | RETENTION TIME | AREA % |
|---|---|---|
| Acetone | 62 seconds | 54.5 |
| Allyl alcohol | 204 seconds | 15.3 |
| Allyl 2-cyclopentenyl ether | 302 seconds | 5.2 |
| 2-Cyclopentenyl acetate | 390 seconds | 19.3 |

| COMPOUND | RETENTION TIME | AREA % |
|---|---|---|
| 2-Cyclopentenol | 422 seconds | 3.6 |
| Acetic acid | 500 seconds | 0.8 |
| 2-Cyclopentenyl ether | 590 seconds | 0.4 |

The mass spectrum of the material having a retention time of 302 seconds was in full agreement with the mixed ether structure assigned to it. No diallyl ether was obtained in this experiment, and it is also noteworthy that very little bis-(2-cyclopentenyl) ether was formed.

EXAMPLE 26

CATALYTIC ALCOHOLYSIS OF 2-CYCLOPENTYL ACETATE BY PASSAGE THROUGH A BED OF ION EXCHANGE RESIN

A solution of 1.80 g (0.014 mol) of 2-cyclopentenyl acetate in 3.80 g (0.12 mol) of methanol and 0.700 g of chlorobenzene (the internal standard for chromatographic analysis) was slowly passed through a jacketed column containing 20 ml of Dowex 1-X4 (an anion exchange resin of the quaternary ammonium type) in the hydroxide form in methanol. The column was maintained at 56° C by refluxing acetone in the jacket. The resin was then rinsed with methanol, and the combined effluent and rinsings were analyzed by gas chromatography using a 6ft. OV-17 column programmed from 80° to 220° C. The analysis showed that 2-cyclopentenol had beend formed in 96% yield and essentially 100% efficiency. No byproducts were observed.

The total residence time of the reaction mixture in the ion exchange resin bed was less than 5 minutes.

EXAMPLE 27

2-CYCLOHEXENYL 2-CYCLOPENTENYL ETHER

A two-phase reaction mixture containing 2-cyclopentenyl acetate (0.30 g, 2.4 millimols), 2-cyclohexenol (0.50 g, 5.1 millimols), tetrabutylammonium hydrogen sulfate (0.020 g, 0.06 millimols), and water (0.25 g, 13.9 millimols) was heated at 40° C with vigorous stirring for four hours. Acetone was then added to give a one-phase system for analytical purposes, and the solution was analyzed by gas chromatography using an Apiezon column programmed from 60 to 220° C. The following relative peak areas were observed for the cyclic components:

| | |
|---|---|
| 2-Cyclopentenol | 5.9 |
| 2-Cyclohexenol | 70.2 |
| 2-Cyclopentenyl acetate | 20.8 |
| Bis-(2-Cyclopentenyl) ether | 0.3 |
| 2-Cyclohexenyl 2-cyclopentenyl ether | 2.8 |
| | 100.0 |

No bis-(2-cyclohexenyl) ether and only a small amount of bis-(2-cyclopentenyl) ether were formed. Although the yield of mixed ether was low (approximately 7% of the theoretical), the chemical efficiency for a process based on this procedure is high since the cyclopentenol, cyclohexenol, cyclopentenyl acetate, and bis-cyclopentenyl ether can all be recycled to increase the yield of mixed ether.

EXAMPLE 28

2-CYCLOPENTENYL 2-METHYLALLYL ETHER

A mixture of 2-cyclopentenyl acetate (0.30 g) and 2-methylallyl alcohol (0.40 g) was stirred vigorously at 40° C for 4.5 hours with a solution of 0.020 g of tetrabutylammonium bisulfate in 0.25 g of water. Acetone was added at the end of the reaction period, and the solution was analyzed by gas chromatography using an Apiezon column programmed at 60–220° C. The yield of 2-cyclopentenyl 2-methyl allyl ether, estimated from peak areas, was 40%. No peaks corresponding to bis-(2-methylallyl) ether or bis-(2-cyclopentenyl) ether were observed.

EXAMPLE 29 n-BUTYL 2-CYCLOPENTENYL ETHER

2-Cyclopentenyl acetate (0.30 g) and n-butanol (0.40 g) were mixed and stirred vigorously at 40° C. for 4 hours with a solution of 0.020 g of tetrabutylammonium hydrogen sulfate in 0.25 g of water. At the end of the reaction period acetone was added to give a single phase, and the solution was analyzed by gas chromatography using an Apiezon column programmed at 60–220° C. Peaks for the cyclic compounds had the following relative areas.

2-Cyclopentenol: 15
2-Cyclopentenyl acetate: 65
Butyl 2-Cyclopentenyl ether: 20

From this it was estimated that the mixed ether had been formed in 17% yield.

EXAMPLE 30

2-CYCLOPENTENYL ISOPROPYL ETHER

2-Cyclopentenol (0.30 g), isopropanol (0.40 g), and an aqueous solution of 0.020 g of tetrabutylammonium hydrogen sulfate in 0.25 g of water were mixed, and the two-phase system was stirred vigorously at 40° C for 4 hours. Acetone was then added to homogenize the mixture, and it was analyzed by gas chromatography. Peaks corresponding to about a 6% yield of 2-cyclopentenyl isopropyl ether and about a 12% yield of 2-cyclopentenol were observed along with a concomitant peak for the co-product acetic acid. No bis-(2-cyclopentenyl) ether was formed.

CONTROL C

ATTEMPTED PREPARATION OF t-BUTYL 2-CYCLOPENTENYL ETHER

A mixture of 2-cyclopentenyl acetate (0.3 g) and t-butanol (0.4 g) was stirred vigorously for 5 hours at 40° C. with a solution of 0.02 g of tetrabutylammonium bisulfate in 0.025 g of water. At the end of the reaction period, acetone was added to homogenize the mixture for analysis by gas chromatography. The only peaks corresponding to cyclic compounds were those corresponding to 2-cyclopentenol (about 20% yield), unreacted 2-cyclopentenyl acetate, and a trace of bis(2-cyclopentenyl) ether. Separate gas chromatographic analyses were conducted using Apiezon (60–220° C) and Carbowax-20M (60–220° C) columns with a thermal conductivity detector and using Carbowax and OV-1 columns in series (60° + 4°/minute) with a flame ionization detector to eliminate interference by the peak for water. In none of these analyses was any peak for t-butyl 2-cyclopentenyl ether observed.

The experiment was repeated using 0.01 g of sodium bisulfate as the catalyst in place of the quaternary ammonium salt. As before, no peak corresponding to t-butyl 2-cyclopentenyl ether was observed in the gas chromatographic analysis.

Although the invention has been described in its preferred form with a certain degree of particularity, it is understood that the present disclosure has been made only by way of example and that numerous changes can be made without departing from the spirit and scope of the invention.

What is claimed is:

1. Method of preparing bis-(2-cyclopentenyl) ether which consists essentially of contacting one part by weight of at least one 2-cyclopentenyl derivative having the formula:

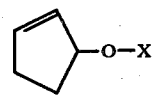

wherein X is

or H and R is H or an alkyl or cycloalkyl having 1 to about 8 carbons or aryl having 6 to 10 carbons with about 0.1 to about 10 parts by weight of an aqueous solution containing about 0.01 to about 2.0 moles per liter of solution of an acid having pKa of about 2 to about 3, at a temperature of about 0° C. to about 100° C.

2. Method claimed in claim 1 wherein X is

3. Method claimed in claim 2 wherein R is methyl.
4. Method claimed in claim 2 wherein R is hydrogen.
5. Method claimed in claim 1 wherein X is H.
6. Method claimed in claim 1 wherein the temperature is about 10 to about 50° C.
7. Method claimed in claim 1 wherein one part of 2-cyclopentenyl derivative is contacted with about 0.2 to 3 parts by weight of aqueous solution.
8. Method claimed in claim 1 wherein the acid is an acid salt of a tertiary amine or quaternary ammonium hydroxide.
9. Method claimed in claim 8 wherein the acid is tetrabutylammonium bisulfate.
10. Method claimed in claim 1 wherein the acid is an alkali metal bisulfate.
11. Method claimed in claim 1 wherein the bis(2cyclopentenyl) ether prepared is separated from the reactants and unreacted 2-cyclopentenyl derivative and aqueous acid solution recycled for further reaction.
12. Method claimed in claim 1 wherein a mixture of 2-cyclopentenyl derivatives is contacted with said aqueous solution.
13. Method claimed in claim 1 wherein the 2-cyclopentenyl derivative is 2-cyclopentenol derived from the 2-cyclopentenyl ester by alcoholysis over a base.
14. Method claimed in claim 13 wherein the alcoholysis is effected with a base consisting of a basic ion exchange resin.

* * * * *